United States Patent [19]

Nelson, deceased

[11] 4,386,931
[45] Jun. 7, 1983

[54] OSTOMY LEAKAGE REPRESSER

[76] Inventor: Vernon L. Nelson, deceased, late of Portland, Oreg., by Bernice A. Nelson, administrator

[21] Appl. No.: 283,445

[22] Filed: Jul. 15, 1981

[51] Int. Cl.³ ............................................. A61F 5/44
[52] U.S. Cl. .................................................. 604/338
[58] Field of Search ............... 128/283, 295, 760, 767; 604/327, 328, 332 (U.S. only), 337, 338, 339, 341, 342, 343

[56] References Cited

U.S. PATENT DOCUMENTS

| | | | |
|---|---|---|---|
| 2,133,130 | 10/1938 | Buchstein | 128/340 |
| 2,796,063 | 6/1957 | Smelser | 128/283 |
| 2,869,547 | 1/1959 | Yohe | 128/283 |
| 3,366,114 | 1/1968 | Kanter | 128/283 |
| 3,523,092 | 10/1970 | Rodgers | 128/283 |
| 4,085,752 | 4/1978 | Canale | 128/283 |
| 4,224,610 | 9/1980 | Quinby | 340/614 |
| 4,319,571 | 3/1982 | Winchell | 128/283 |

FOREIGN PATENT DOCUMENTS

| | | | |
|---|---|---|---|
| 533665 | 12/1954 | Belgium | 128/283 |
| 187101 | 7/1907 | Fed. Rep. of Germany | 128/283 |
| 1274374 | 5/1972 | United Kingdom | 128/283 |

Primary Examiner—Richard J. Apley
Assistant Examiner—J. L. Kruter
Attorney, Agent, or Firm—Victor J. Evans & Co.

[57] ABSTRACT

Disclosed herein is an ostomy leakage represser adapted to place a diversion pouch in good sealing engagement with a stoma implanted in the user, the represser being suitably fashioned to provide pressure along a lower surface of the stoma so as to effectively eliminate any leakage that normally occurs. The represser includes a belt connected to a body portion having substantially triangular shape, an apex of a body portion provide with a circumferential lip having in a preferred form an open gap along a top area adapted to frictionally engage an annular spacer provided on most diversion pouches, the body portion suitably formed to provide pressure on an area below the stoma so that a good seal is effected between a flanged opening on the diversion pouch while simultaneously providing a pressure area below the stoma to assure complete drainage.

10 Claims, 3 Drawing Figures

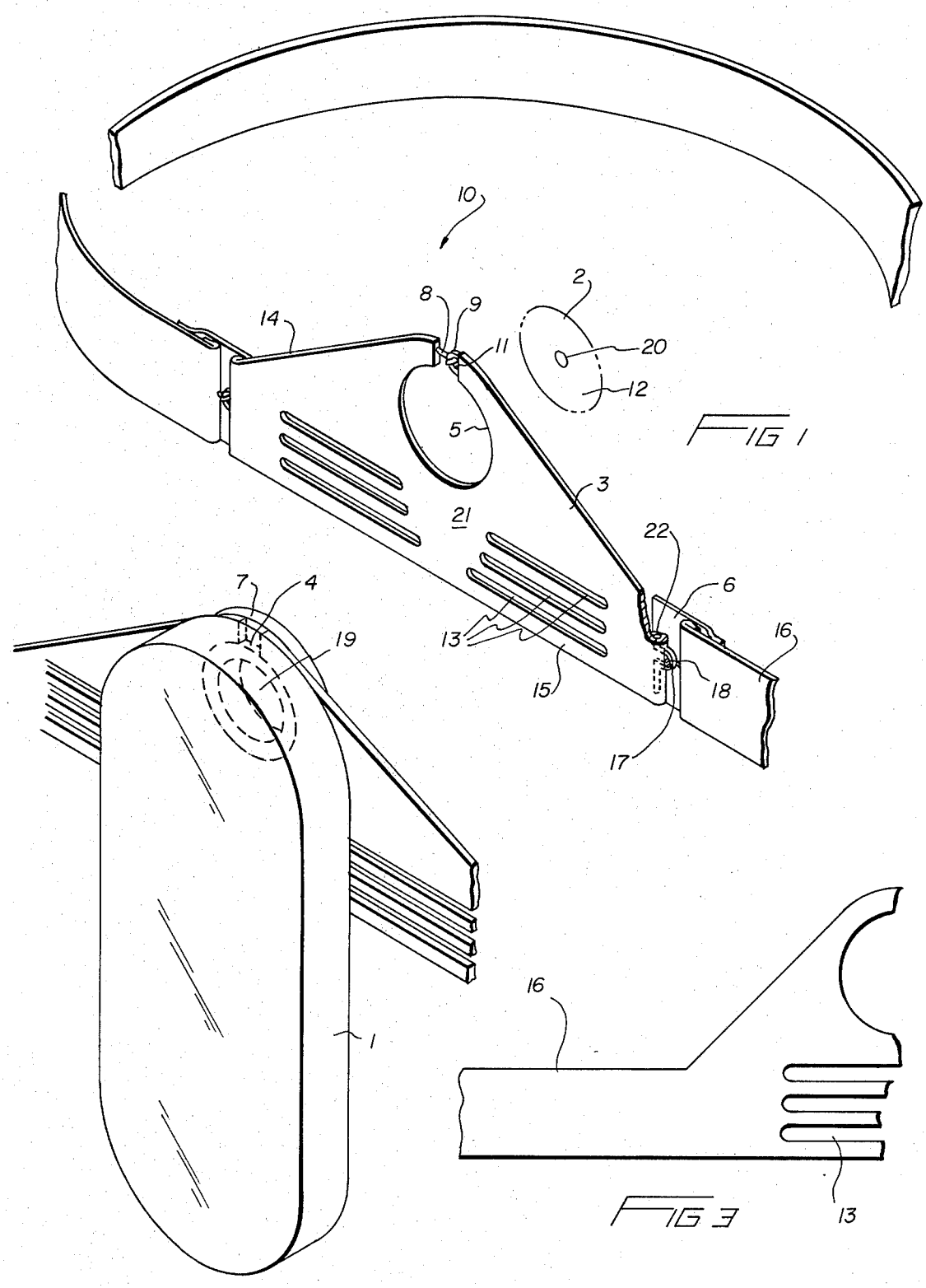

OSTOMY LEAKAGE REPRESSER

BACKGROUND OF THE INVENTION

This invention relates generally to devices for discharging fluids from a stoma area implanted surgically in the body of a patient to a collection or diversion pouch in such a manner that a tight seal is effected between the interface of the pouch and the stoma to retard and discourage any leakage.

While advances in surgical technology have allowed people with urinary tract problems to conduct relatively normal lives, a crying need exists for an ostomy leakage suppressor which provides a positive seal between the stoma and the diversion pouch so that unwanted migration of urinary fluids does not occur along the body skin area, thereby contaminating the associated environment.

In this regard, applicant is aware of the following patents which appear to reflect the state of the art in so far as these references appear to be germane to the patent process:

U.S. Pat. No. 2,133,130—Buchstein
U.S. Pat. No. 2,869,547—Yohe
U.S. Pat. No. 3,532,092—Rodgers
U.S. Pat. No. 4,224,610—Quinby Of these patents, Buchstein is of great interest in that he teaches the use of a supra pubic drainage appliance in which an attachment (FIG. 10) is made by means of a tube 15 extending into a pouch 23 supported on one's leg, the attachment 15 made and retained by means of a belt.

Rodgers teaches the use of a urinary appliance for use with a stoma of a diverted ureter and includes a relatively rigid shell like collector juxtapositionable over the stoma for capturing urinal drainage and having a peripheral seal maintained by a wide abdominal belt from which is suspended a pubic area reservoir communicating with a drainage trap of the collector, and in which filling of the reservoir causes expansion and tends to produce a negative pressure in the collection system to insure drainage for the diverted ureter. In Rodgers, the entire inner wall portion (28) along with the sealing area (30) FIG. 6, is placed in close proximity to the stoma by means of belt tension.

Quinby teaches the use of an alarm device for a drainage pouch in which a signal is provided responsive to expansion of the pouch when the pouch becomes filled.

The remaining reference shows the state of the art further.

By way of contrast, the instant application is directed to an ostomy leakage represser in which a support means for detachably engaging the diversion pouch takes the form of a circumferential lip adapted to tightly engage an annular spacer provided on the diversion pouch between the pouch reservoir and flanged opening in which the lip is provided in one form with an opening on the top area, and the lip is carried on a body portion having a substantially triangular configuration in which the truncated apices of the lowermost portion of the triangle connect to a belt in such a manner that wearing the belt provides a pressure gradiant on the stoma which experiences increased pressure along a bottom portion of the stoma along the intersecting area of the flanged opening so as to provide a better seal at that area and to encourage discharged urine to enter the flanged opening thereon to the diversion pouch.

SUMMARY AND OBJECTS OF THE INVENTION

Accordingly, this invention has as an objective to provide an ostomy leakage represser which is not fraught with the difficulties associated with the prior art.

Additionally, it is an object of this invention to provide a device of the character described above in which a positive seal exists between the stoma and the flanged opening of a diversion pouch by providing a pressure gradiant along a lower portion of the stoma and the associated bearing surface of the flanged opening.

It is yet a further object of this invention to provide a device of the character described above which can be worn in comfort by the user and is relatively adjustable to provide leakage suppression for people of all sizes.

It is yet a further object of this invention to provide a device of the character described above which is relatively inexpensive to manufacture, extremely durable in construction, and safe to use, and lends itself to mass production techniques.

It is yet a further object of this invention to provide a device of the character described above which while providing a pressure gradiant on the stoma, does not provide an associated unwanted bothersome pressure on the area touched by the belt and body portion of the support so that discomfort is not experienced.

It is still another object of this invention to provide a device of the character described above which is readily dissociated from the diversion pouch and adjustable so as to facilitate expeditious removal and replacement of the diversion pouch.

These and other objects will be made manifest when considering the following patent specification when taken in conjunction with the appended drawing figures.

BRIEF DESCRIPTION OF THE DRAWING FIGURES

FIG. 1 is a perspective view of the ostomy leakage repressing device according to the present invention;

FIG. 2 is a perspective view of a portion of the represser with the diversion pouch associated therewith; and FIG. 3 is a fragmentary view of the device according to the present invention showing an alternative form.

BRIEF DESCRIPTION OF THE PREFERRED EMBODIMENT

Referring to the drawings now, wherein like references numeral refer to like parts throughout the various drawing figures, reference numeral 10 is directed to the ostomy leakage represser according to the present invention.

The represser 10 is suitably formed to accommodate a diversion pouch 1 of any convenient shape, but the represser is specifically designed to engage diversion pouch 1 which has a flanged opening 7 separated from the pouch by an annular spacer 4, and an opening 19 extending through the spacer and the flange as best seen in FIG. 2.

The diversion pouch 1 is adapted to have the opening 19 register with an orifice 20 located on a stoma 2 embedded in the user, a surgical technique well known. In order to support the pouch 1 so that the bearing surface between the stoma 2 and the flange 7 is a tight fit, thereby minimizing the likelihood of unwanted seepage along the interface, the represser 10 according to the present invention is provided.

The represser 10 includes a support means for detachably engaging the spacer 4 and includes a belt 16 adapted to gird the user whereby the support means alters the pressure pattern associated with the bearing surface of the flanged opening 7 against the stoma 2. Heretofore, the pressure has been thought to be uniformly deployed along the flanged area, but the inventor advises that an increased pressure along a bottom area 12 of the stoma will retard the migration of fluid coming from the stoma in such a manner as to assure disposition within the pouch 1.

Specifically, the support means includes a circumferential 5 surrounding the annular spacer 4, the lip 5 having a gap along a top edge thereof, and the support means has the form of a triangle whose apices are truncated. The gap around the lip 5 is defined by first and second termini 11 facing one another in such a manner that latching means are included for the selective engagement of the termini. Specifically, the latching means in a preferred form is defined by an eyelet 9 disposed on one termini adapted to coact with a clasp or hook 8 on an opposing termini in such a manner that any exposed protrusions of the inter engagement of the latching means extends outwardly away from the body of the patient. Alternatively, the gap may be left as a free opening and the material forming the support means 3 would have sufficient resiliency and memory to retain a frictional fit on the spaced flange 4, many plastics of which would perform this function.

As shown in the drawings, the lip 5 is integrally formed on an upper apex of a substantially triangular shaped support means body portion 3 which has a base 15 and side edges 14 formed in such a manner that all of the apices are somewhat truncated.

It is contemplated that the body portion 3 be provided with a plurality of laterally extending elongate slots 13 so as to increase the comfort of the wearer by providing ventilation areas and the absence of pressure areas on the body. In a preferred form, two sets of elongate slots 13 are provided offset from the lip in such a manner that an imperforate area 21 is provided directly below the lip 5 for additional benefits.

It is to be noted that the width of the belt 16 is such that its width is coextensive with the chord length of the truncated lower apices so that the sides 14 extend up above the width of the belt. In this manner therefore by adjusting the tightness of the belt, the imperforate area 21 provides a pressure gradiant on the stoma specifically around area 12 so that the lower portion of the stoma has a greater pressure bearing surface than an upper portion by virtue of the configuration of the belt.

In one form of the invention, the belt is shown as being integral with the body portion 3 (FIG. 3), but in another form, the belt can be detachable from the body portion and in addition the length of the belt can be adjusted magnitude. For this purpose, the truncated lower apices of the body portion are provided with eyelets 17 embedded and fastened into the lower apex of the body portion, the body portion having a folded over area 22 to support the eyelet 17. Associated with the belt 16 a clasp 18, in a preferred form of hook shaped configuration, is adapted to engage the eyelet 17 of the body portion, although the two components could be inter changed as is well known in the art. Since the belt which girds the patient defines the pressure area, it is found desirable to provide a protective shroud 6 disposed between the user and the clasp and eyelet to disperse the pressures associated along that area.

Having thus described the invention is should apparent that numerous structural modifications are contemplated as being part of this invention as described hereinabove and defined hereinbelow by the claims.

What is claimed is:

1. An ostomy leakage represser comprising in combination:
   a diversion pouch having a flanged opening on an upper portion thereof, said flanged opening removed from said pouch by an annular spacer,
   support means for detachably engaging said spacer including a belt means having a lower portion disposed at an elevation lower than the flanged opening adapted to girth the user and an upper portion defined by an apex having an opening means to provide a resilient frictional fit with the flanged opening and the lower portion below the flanged opening communicating with said belt means whereby said support means alters the pressure associated with the bearing surface of the flanged opening adapted to be used against a stoma embedded in the patient by providing greater pressure on a lower portion of the stoma induced by said lower portion of said belt means to provide a leak resistant seal through better support.

2. The device of claim 1 wherein said support means includes a circumferential lip surrounding the annular spacer.

3. The device of claim 2 wherein said support means further includes a gap on a top portion of said lip having latching means for altering said lip and its dimension.

4. The device of claim 3 wherein said lip is integrally formed on an said upper apex of a substantially triangular shaped support means body portion.

5. The device of claim 4 wherein said body portion includes an imperforate area below said lip to apply increased pressure through said belt to an area below the stoma.

6. The device of claim 6 wherein said body portion includes laterally extending elongate slot means disposed on either side of said imperforate area to provide ventilation to the user's body.

7. The device of claim 6 wherein said body portion has two lower apices which are truncated and attached to said belt.

8. The device of claim 7 wherein said latching means comprises an eyelet on one terminal of said lip top portion and a clasp directed away from the user on another terminal of said lip top portion.

9. The device of claim 8 wherein said belt attaches to said apices via eyelets on said apices and clasps on ends of said belt which are directed away from the user, and a protective shroud between said user and said clasp and eyelet.

10. The device of claim 8 wherein said belt has the same width as the vertical height of said truncated lower apices to enhance the pressure gradient; sides extending from said truncated lower apices to said upper apex of said triangular shaped support means body portion experiencing less pressure from said belt as said sides extend to said upper apex.

* * * * *